(12) United States Patent
Hahn

(10) Patent No.: US 8,398,613 B1
(45) Date of Patent: Mar. 19, 2013

(54) METHOD AND APPARATUS FOR DRAINING FLUID FROM AN ORGANISM

(76) Inventor: Michael R. Hahn, Oklahoma City, OK (US)

( * ) Notice: Subject to any disclaimer, the term of this patent is extended or adjusted under 35 U.S.C. 154(b) by 616 days.

(21) Appl. No.: 12/019,516

(22) Filed: Jan. 24, 2008

(51) Int. Cl.
*A61M 27/00* (2006.01)
(52) U.S. Cl. ............ 604/541; 604/101.01; 604/101.03; 604/101.05; 604/528; 604/102.01; 604/540; 606/192; 606/194
(58) Field of Classification Search ................ 604/540, 604/541
See application file for complete search history.

(56) References Cited

U.S. PATENT DOCUMENTS

| | | | |
|---|---|---|---|
| 3,416,532 A * | 12/1968 | Grossman | ............ 604/267 |
| 3,528,427 A | 9/1970 | Sheridan et al. | |
| 4,257,422 A | 3/1981 | Duncan | |
| 4,398,910 A | 8/1983 | Blake et al. | |
| 4,778,446 A | 10/1988 | Jensen | |
| 4,781,678 A | 11/1988 | deCouet et al. | |
| 5,024,615 A | 6/1991 | Buchel | |
| 5,045,075 A | 9/1991 | Ersek | |
| 5,336,177 A | 8/1994 | Marcus | |
| 5,597,377 A | 1/1997 | Aldea | |
| 6,547,761 B2 | 4/2003 | Liu | |
| 6,579,271 B1 | 6/2003 | Aruffo et al. | |
| 6,881,204 B1 | 4/2005 | Bunce | |
| 7,125,402 B1 | 10/2006 | Yarger | |
| 7,131,965 B1 | 11/2006 | Thornbury et al. | |
| 7,182,758 B2 | 2/2007 | McCraw | |
| 7,223,263 B1 | 5/2007 | Seno | |
| 7,252,659 B2 | 8/2007 | Shehada et al. | |
| 7,267,671 B2 | 9/2007 | Shehada | |
| 2006/0241689 A1 | 10/2006 | Leiboff et al. | |
| 2007/0185380 A1 | 8/2007 | Kucklick | |

* cited by examiner

*Primary Examiner* — Tatyana Zalukaeva
*Assistant Examiner* — Ilya Treyger
(74) *Attorney, Agent, or Firm* — Tomlinson Rust McKinstry Grable

(57) ABSTRACT

A surgical drain and method for using the same. The surgical drain comprises a first end, which may be sized for placement within an organism. The first end features a plurality of segments, each labeled with an alphanumeric character. The first end may be cut at a line between two of the segments. The alphanumeric character at the terminal end of the first end after cutting is recorded prior to placing the drain within the organism. When removing the drain, the recorded alphanumeric character is compared with the character at a terminal end of the first end of the surgical drain. Thus, a treating professional can ensure that no portion of the surgical drain is left within the wound, preventing infection due to a foreign object left within the organism.

4 Claims, 3 Drawing Sheets

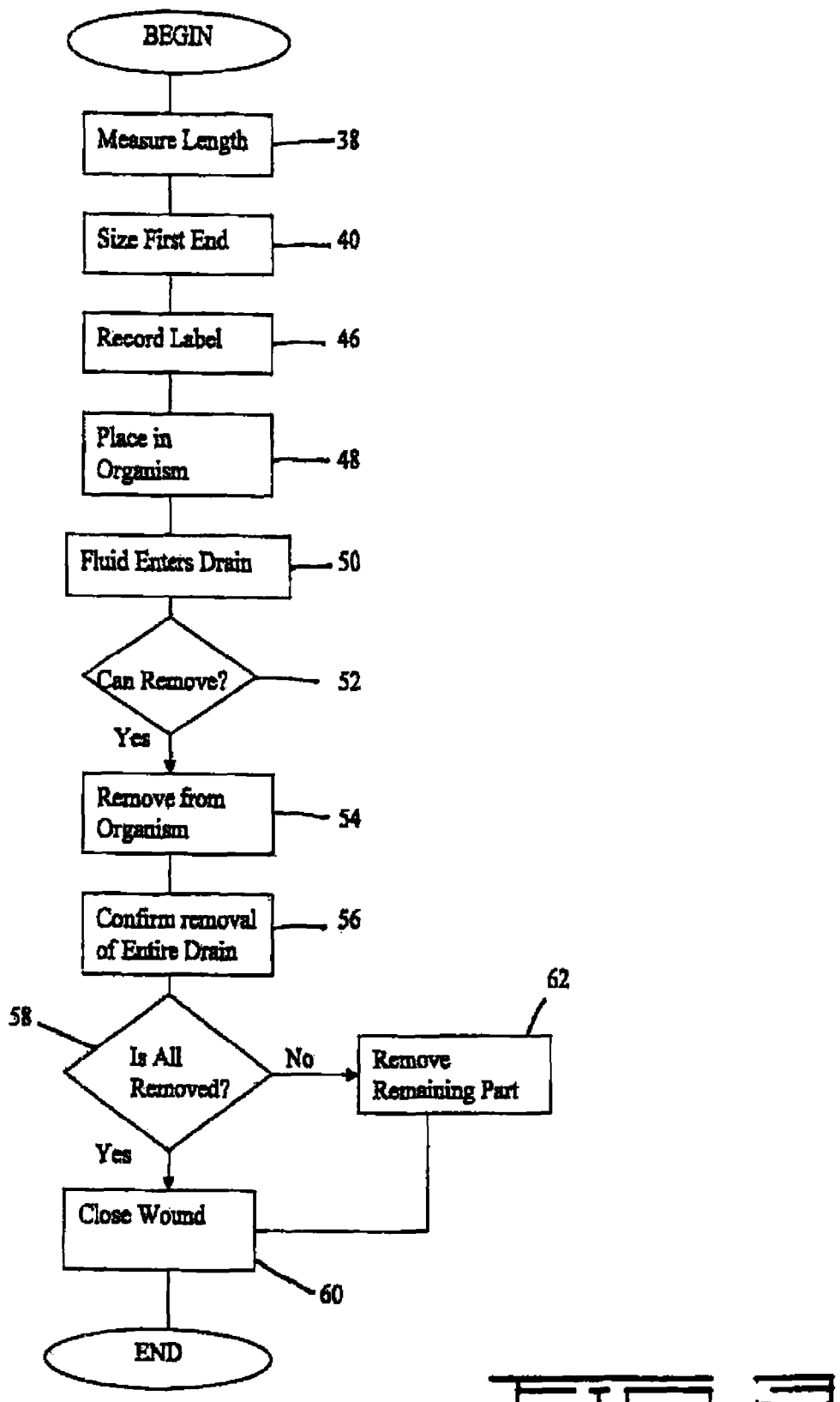

METHOD AND APPARATUS FOR DRAINING FLUID FROM AN ORGANISM

FIELD OF THE INVENTION

The present invention is directed to surgical drains and methods for using the same, for use in medical applications.

SUMMARY OF THE INVENTION

The present invention is directed to surgical drains and methods for using the same, for use in medical applications. The method comprises the steps of providing a surgical drain, measuring a desired length of a first end of the drain to be placed inside the organism, sizing the first end, then recording a distal alphanumerically labeled segment of the first end, and placing the first end of the surgical drain within the organism. The surgical drain comprises the first end and a second end. The first end is adapted for use within the organism and comprises a plurality of alphanumerically labeled segments. The first end is sized to the desired length by removing an excess amount of the first end. The second end is positionable outside the organism.

Another embodiment of the present invention is directed to a surgical drain. The surgical drain comprises a first end and a second end. The first end comprises a plurality of alphanumerically labeled segments. The first end is adapted for use within an organism. The second end is positionable outside the organism.

Yet another embodiment is directed to a surgical drain. The surgical drain comprises a first end and a second end. The first end comprises a plurality of Arabic letter labeled segments. The first end is adapted for use within an organism. The second end is positionable outside the organism.

Another embodiment of the present invention is directed to a method for removing fluid from an organism. The method comprises the steps of providing a surgical drain comprising a first end and a second end, measuring a desired length of the first end, to be placed inside the organism, sizing the first end, recording a terminal alphanumerically labeled segment, placing the first end of the surgical drain within the organism, removing the first end of the surgical drain from the organism after fluid removal, and confirming removal of the terminal alphanumerically labeled segment. The first end comprises a plurality of the alphanumerically labeled segments. The first end is adapted for use within the organism. The first end is sized to the desired length by removing an excess amount of the first end to create the terminal alphanumerically labeled segment. The first end is placed within the organism to remove fluid with the terminal alphanumerically labeled segment inside the organism. Removal of the segment is confirmed by matching an alphanumeric character present at a terminal end of the removed surgical drain to the character present on the terminal alphanumerically labeled segment. The second end is positionable outside the organism.

BRIEF DESCRIPTION OF THE DRAWINGS

FIG. 3 is a diagrammatic representation of a method for using a surgical drain in accordance with the present invention.

DETAILED DESCRIPTION OF THE PREFERRED EMBODIMENTS

Surgical drains are tubes used to remove blood, pus, or other bodily fluid from a location in an organism. Accumulated fluid in a wound causes swelling and provides a location for bacteria to accumulate. Accumulated bacteria may cause a secondary infection at the wound location. This secondary infection is often unrelated to the reason for the accumulated fluid, but the result may be a serious health risk. Therefore, while proper drainage of a wound does not directly treat the underlying cause of accumulating fluid, it is a critical part of treatment, as it prevents serious, and perhaps deadly, secondary infections.

One potential hazard with the use of surgical drains is the risk that a portion of the surgical drain may tear away from the drain during removal and accidentally be left inside a wound. The portion of the drain left in the organism may cause infection. This situation may occur because stitches are often used inside the wound near the surgical drain to promote healing. However, it is possible for a stitch to be accidentally placed through the internal portion of the surgical drain itself. This stitch may cause the drain to tear upon removal and result in a portion remaining within the organism.

Surgical drains are often removed by simply pulling the drain out through the wound's opening. The internal portion of the surgical drain, as will be described in more detail below, is often heavily perforated to enhance fluid flow into the drain. This also weakens the drain such that when it is pulled, force due to the tear is virtually undetectable. A portion of the drain may be left inside the body after the wound is closed. A foreign object such as a surgical drain may cause infection, requiring further medical attention and increasing the risk to patients. Thus, a need exists for a simple, reliable way to ensure no foreign object, such as a portion of the surgical drain remains in a wound after treatment is completed.

Figure 1:
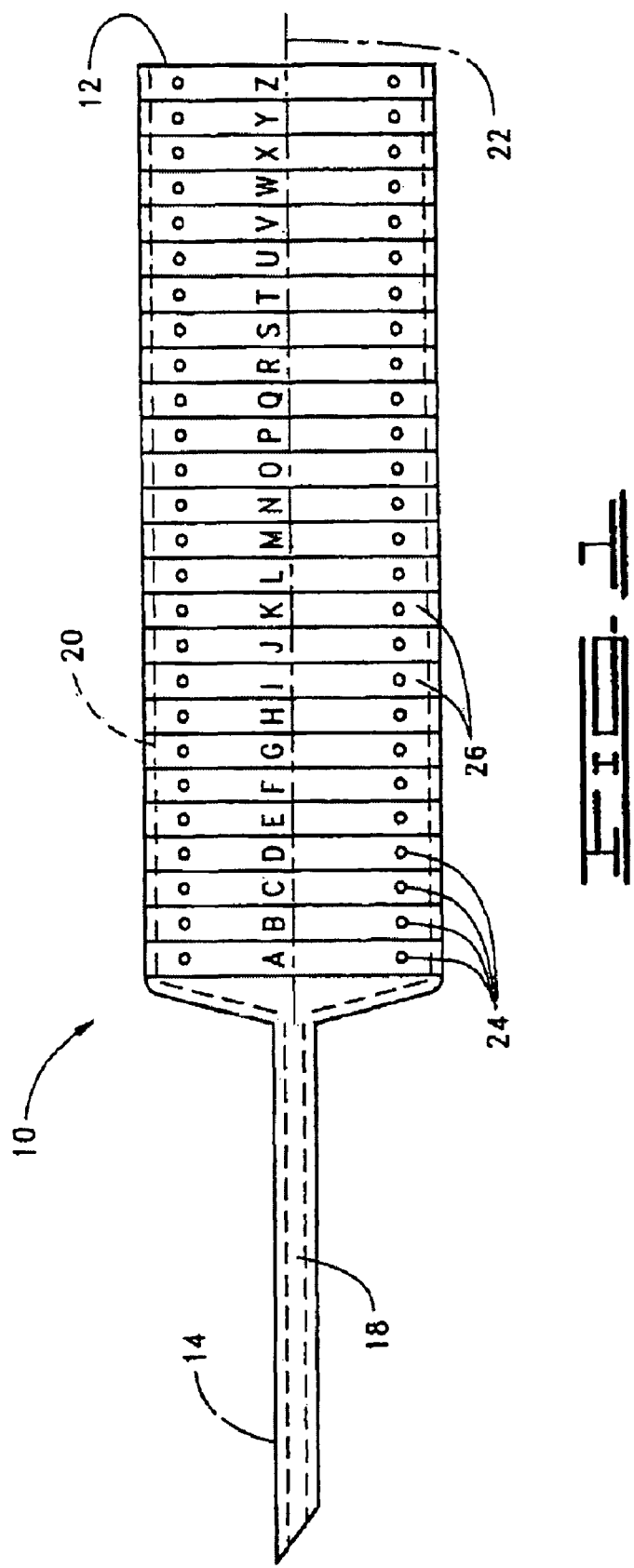
FIG. 1 is a side view of a surgical drain of the present invention having alphanumerically labeled segments.

Turning now to the drawings in general and FIG. 1 in particular, shown therein is a surgical drain 10. The surgical drain 10 comprises a first end 12 and a second end 14. The first end 12 is adapted for use within an organism 16 (shown in FIG. 2). The second end 14 is positionable outside of the organism 16. The second end 14 may comprise a cylindrical drain tube 18 or other apparatus for transporting fluid from the organism 16 in a sanitary fashion. The drain tube 18 may be adapted to deposit drained fluid into a reservoir using gravity, or alternatively may be adapted for connection to a suction means or other mechanism for mechanically removing fluid.

The first end 12 of the surgical drain 10 comprises a lumen 20 having a longitudinal axis 22. A plurality of perforations 24 are dispersed along the lumen 20. Preferably, the perforations 24 are disposed in a radial orientation relative to the longitudinal axis 22 of the lumen 20. These perforations 24 allow fluid located inside the organism 16 to enter the lumen 20 and exit the organism through the surgical drain 10.

Figure 2:
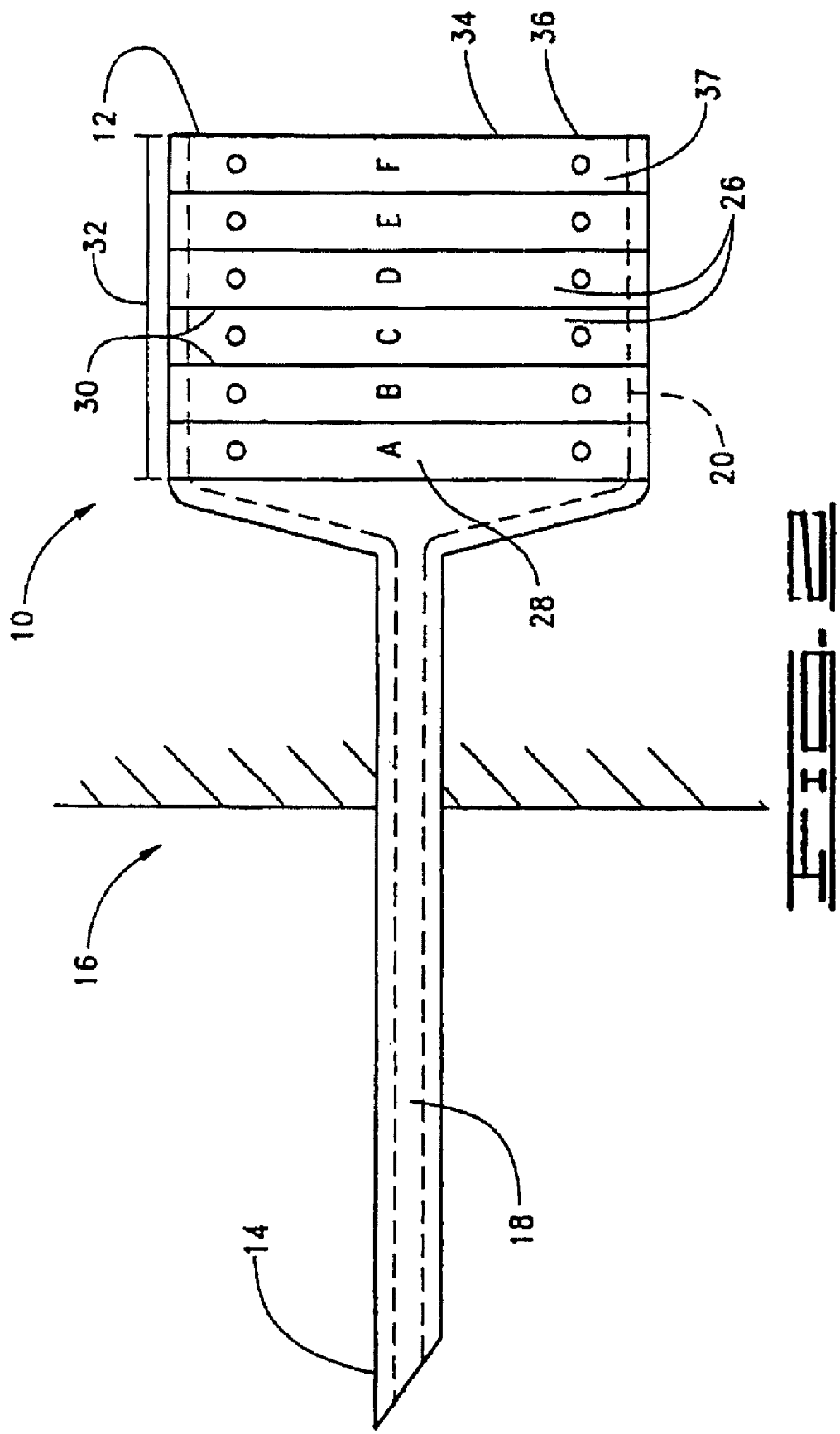
FIG. 2 is a side view of the surgical drain of FIG. 1 having been cut and inserted into an organism.

With reference now to FIG. 2, the first end 12 further comprises a plurality of labeled segments 26. The segments 26 may be labeled with a plurality of unique alphanumeric characters 28. Alternatively, the segments 26 may be labeled with Arabic characters, colors, roman numerals, or any other identifying characteristic. The characters 28 may comprise a series of sequentially arranged letters or sequentially arranged numbers. The characters 28 may also comprise numerical representations of length as depicted on a ruler printed upon the surgical drain 10. Each of the labeled segments 26 may comprise a plurality of lines 30 disposed to define boundaries between adjacent segments. The lines 30 define a location at which the first end 12 may be cut to size the first end to a desired length 32. When the first end has been cut to reach the desired length 32, the first end terminates at a terminal end 34. The line 30 at which the first end 12 is cut defines a terminal line 36, located at the terminal end 34 of the first end of the surgical drain 10. The segment 26 proximate the terminal line 36 defines the terminal, or distal, labeled segment 37.

In operation, as depicted in FIG. 3, the surgical drain 10 may be utilized to remove fluid from an organism 16 (FIG. 1), lessening the risk of leaving a portion of the surgical drain within the organism. First, the desired length 32 (FIG. 2) of the first end should be measured at step 38 based on the needs of the particular organism 16 from which fluid is to be drained. Next, the first end 12 (FIG. 1) is sized at step 40 by removing an excess amount of the first end. The sizing may be accomplished at step 40 by cutting the first end 12 of the surgical drain 10 so that the line 30 at which the first end 12 is cut defines the terminal line 36.

After sizing at step 40, the alphanumeric or other character 28 located on the terminal labeled segment 37 is recorded at step 46. Preferably, the character 28 is recorded on the patient's chart or a similar location where it will be readily available for a treatment professional. Additionally, the character 28 may be recorded on the drain tube 18 of the surgical drain 10.

Upon recording the alphanumeric character 28 corresponding to the terminal labeled segment 37 at step 46, the first end 12 of the surgical drain 10 is placed within the organism 16 at step 48. At step 48, the terminal labeled segment 37 is within the organism 16. At step 50, fluid enters the surgical drain 10 through the perforations 24 in the lumen 20 of the first end 12, and exits the surgical drain through the drain tube 18 of the second end 14, outside of the organism 16.

The surgical drain 10 may remain within the organism 16 until a treatment professional determines it is appropriate to remove it at step 52, either for replacement, cleaning or at the termination of the organism's need for the surgical drain. Therefore, after fluid removal at step 50 and termination of the need for the surgical drain 10 at step 52, the first end 12 of the surgical drain is removed from the organism 16 at step 54. Immediately after removal at step 54 of the first end 12, removal of the entire surgical drain 10 may be confirmed at step 56 by matching the character 28 of a labeled segment 26 located at a terminal end 34 of the removed surgical drain 10 with the recorded labeled segment 37.

If at step 58 it is confirmed that the entire surgical drain 10 is removed, the wound within which the surgical drain was placed may be closed at step 60. If matching the character 28 of the labeled segment 26 present at the terminal end 34 of the removed surgical drain 10 with the recorded labeled segment 37 at step 58 reveals that a portion of the first end 12 remains within the organism 16, a treating professional can immediately take steps to remove the remaining portion at step 62.

Various modifications can be made in the design and operation of the present invention without departing from the spirit thereof. Thus, while the principal preferred construction and modes of operation of the invention have been explained in what is now considered to represent its best embodiments, which have been illustrated and described, it should be understood that the invention may be practiced otherwise than as specifically illustrated and described.

What is claimed is:

1. A method for removing fluid from an organism while insuring complete removal of foreign objects from the organism, the method comprising:
    providing a surgical drain, the surgical drain comprising:
        a first end comprising a plurality of alphanumerically labeled segments, wherein the first end is adapted for use within the organism; and
        a second end positionable outside the organism; and
    measuring a desired length of the first end to be placed inside the organism;
    sizing the first end to the desired length by cutting off an excess amount of the first end before placing the first end of the surgical drain within the organism;
    recording a distal alphanumerically labeled segment of the first end after sizing of the first end; and
    placing the first end of the surgical drain within the organism.

2. The method of claim 1 wherein each of the plurality of alphanumerically labeled segments comprises a plurality of lines disposed to define a boundary between adjacent segments.

3. The method of claim 1 further comprising removing the first end of the surgical drain from the organism; and confirming the entire amount of the first end of the surgical drain has been removed from the organism by matching the alphanumerically labeled segment disposed at a terminal end of the removed surgical drain to the recorded alphanumerically labeled segment.

4. A method for removing fluid from an organism comprising:
    providing a surgical drain, the surgical drain comprising:
        a first end comprising a plurality of alphanumerically labeled segments, wherein the first end is adapted for use within the organism; and
        a second end positionable outside the organism; and
    measuring a desired length of the first end to be placed inside the organism;
    sizing the first end to the desired length by cutting off an excess amount of the first end to create a terminal alphanumerically labeled segment before placing the first end of the drain within the organism;
    recording the terminal alphanumerically labeled segment;
    placing the first end of the surgical drain within the organism to remove fluid with the terminal alphanumerically labeled segment inside the organism;
    removing the first end of the surgical drain from the organism after fluid removal and;
    confirming removal of the terminal alphanumerically labeled segment by matching an alphanumeric character present at a terminal end of the removed surgical drain to the character present on the terminal alphanumerically labeled segment.

\* \* \* \* \*